(12) United States Patent
Charbel et al.

(10) Patent No.: US 7,333,848 B2
(45) Date of Patent: Feb. 19, 2008

(54) METHOD AND SYSTEM FOR EVALUATING VERTEBROBASILAR DISEASE

(75) Inventors: Fady T. Charbel, River Forest, IL (US); Fady Charbel, II, River Forest, IL (US); Meide Zhao, Lisle, IL (US); Anthony Curcio, River Forest, IL (US); Sepideh Amin-Hanjani, Chicago, IL (US)

(73) Assignee: Vassol Inc., Chicago, IL (US)

( * ) Notice: Subject to any disclaimer, the term of this patent is extended or adjusted under 35 U.S.C. 154(b) by 287 days.

(21) Appl. No.: 11/049,618

(22) Filed: Feb. 2, 2005

(65) Prior Publication Data

US 2006/0173281 A1 Aug. 3, 2006

(51) Int. Cl.
*A61B 5/05* (2006.01)
(52) U.S. Cl. ............... 600/419; 600/410; 600/411; 600/509; 324/306; 324/307; 324/309
(58) Field of Classification Search ............... 600/410, 600/411, 419, 509; 324/306–307, 309
See application file for complete search history.

(56) References Cited

U.S. PATENT DOCUMENTS

2002/0161292 A1* 10/2002 Wintermark et al. ....... 600/407

FOREIGN PATENT DOCUMENTS

RU 2195178 C2 * 12/2002

OTHER PUBLICATIONS

Reinhardt F et al. Thrombolysis and decompressive surgery in ischemic brain infarction. Neurology Psychiatry and Brain Research. 5(4). Abstract. 1998.*

Sakoh M et al. Cerebral blood flow and blood volume measured b magnetic resonance imaging bolus tracking after acute stroke in pigs: comparison with [(15)O]H(2)O positron emission tomography. Stroke. 31 (8) Abstract. Aug. 2000.*

Kilpatrick M et al. CT-based assessment of acute stroke: CT, CT angiography, and xenon-enhanced CT cerebral blood flow. Stroke. Abstract. 2001.*

Charbel et al. A patient-specific computer model to predict outcomes of the balloon occlusion test. J. Neurosurg. 101:977-988. Dec. 2004.*

Kato T et al. Contrast-Enhanced 2D Cine Phase MR Angiography for Measurement of Basilar Artery Blood FLow in Posterior Circulation Ischemia. AJNR Am J Neuroradiol. 23:1346-1351. Sep. 2002.*

Zhao M et al. Improved phase-contrast flow quantification by three-dimensional vessel localization. Magnetic Resonance Imaging 18:697-706. 2000.*

Armin-Hanjani et al. Use of Quantitative Magnetic Resonance Angiography to Stratify Stroke Risk in Symptomatic Vertebrobasilar Disease. Atroke. 36:1140-1145. May 12 2005.*

* cited by examiner

*Primary Examiner*—Eleni M Mercader Mantis
*Assistant Examiner*—Parikha S. Mehta
(74) *Attorney, Agent, or Firm*—Schwegman, Lundberg & Woessner, P.A.; J. Kevin Parker

(57) ABSTRACT

A method and system are disclosed for evaluating symptomatic VBD which uses quantitative hemodynamic assessment in order to identify patients at high risk for stroke and provide appropriate guidance for intervention. Patients with symptomatic VBD may be considered for intervention to provide blood flow augmentation if evidence of sufficient flow compromise is present as defined by specific flow criteria, and treated medically otherwise.

16 Claims, 2 Drawing Sheets

METHOD AND SYSTEM FOR EVALUATING VERTEBROBASILAR DISEASE

BACKGROUND

Atherosclerotic disease of the vertebrobasilar system is an important etiology of posterior circulation stroke. As compared with the anterior circulation, large or small vessel occlusive disease is a more prevalent source of stroke than thromboembolism. Symptomatic vertebrobasilar disease (VBD), particularly if it affects intracranial vessels, carries a high stroke risk averaging 10-15% per year despite medical therapy. Advances in technology, especially in the arena of endovascular therapy have created new options for treatment of VBD. However, the selection criteria for appropriate candidates for either surgical or endovascular revascularization has been problematic.

SUMMARY

Described herein is a management algorithm for symptomatic VBD which uses quantitative hemodynamic assessment in order to identify patients at high risk for stroke and provide appropriate guidance for intervention. In one embodiment, the hemodynamic assessment is performed by quantitative magnetic resonance imaging, which is a non-invasive tool for measuring blood flow in vessels. Patients with symptomatic VBD may be considered for intervention to provide blood flow augmentation if evidence of sufficient flow compromise is present as defined by specific flow criteria, and treated medically otherwise.

DETAILED DESCRIPTION

Figure 1:
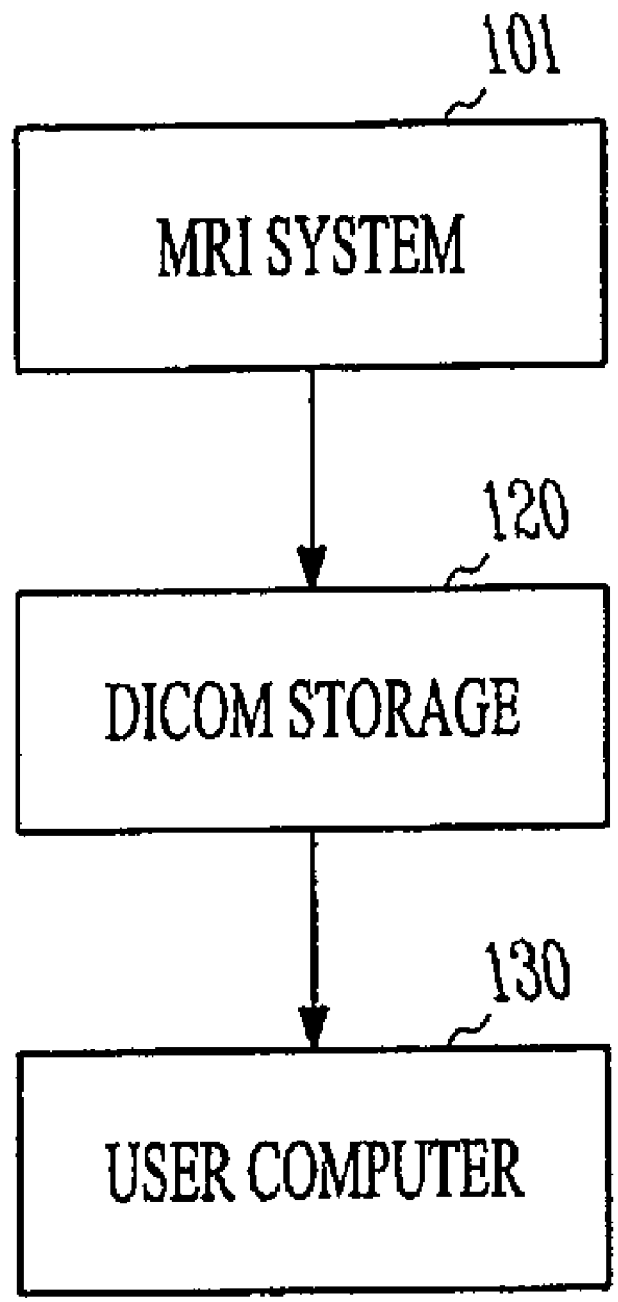
FIG. 1 is a diagram of the components making up an example system.

The present disclosure deals with a system and method for evaluating patients with symptomatic VBD in order to guide their subsequent treatment. Symptoms in the setting of VBD are often the result of local perforator ischemia or regional hypoperfusion secondary to large vessel disease, with low flow states accounting for 30-50% of strokes in the vertebrobasilar distribution. Thromboembolic artery-to-artery embolic events, which are a prominent feature of carotid stenosis, are less commonly encountered in the posterior circulation. The anatomy of collateral vessels in the posterior circulation is such that stenosis in one vertebral artery may be compensated by the other, or by flow through the posterior communicating arteries. As a result severe stenosis may not cause significant flow reduction in the distal territory. Patients without distal flow compromise may still remain at risk for stroke via local perforator ischemia/small vessel disease or emboli, but interventions to augment flow would be less likely to alter the risk of stroke in such patients.

Various imaging modalities including single photon emission computed tomography (SPECT), Xenon CT, MRI, transcranial Doppler (TCD), or PET have bee used to assess the hemodynamic significance of cerebrovascular occlusive disease. Although these modalities have proven valuable in assessment of anterior circulation compromise, they have been less useful in identifying cerebrovascular compromise in VBD. As a result, decision making in the management of VBD has heretofore been primarily based upon the degree of stenosis, with those above 50 to 70% felt to be "hemodynamically significant." Given that the methods utilized for demonstration of hemodynamic compromise in the anterior circulation have been difficult to apply to the posterior circulation, the present disclosure asserts that direct measurement of blood flow in the vertebrobasilar tree using quantitative phase contrast magnetic resonance provides information regarding the hemodynamic effects of VBD and provides a way to differentiate patients most likely to benefit from revascularization.

In accordance with the present method, blood flows are measured at one or more sites distal to where disease may be expected to be present in a patient with symptomatic VBD, including the basilar artery and the posterior cerebral arteries (PCAs). Symptomatic VBD may be characterized by a variety of criteria. An exemplary set of criteria for defining symptomatic VBD is if the patient presents with greater than 50% vertebrobasilar stenosis or occlusion on angiography or MRA and symptoms characterized by symptoms of dizziness or vertigo, transitory bilateral motor or sensory deficits, ataxia or clumsiness, dysarthria, dysphagia, or transitory diplopia or other visual symptoms. A decision-making algorithm utilizing blood flow measurements is then employed to stratify patients with symptomatic VBD into two groups depending upon whether or not distal flow compromise is present. Patients with no distal flow compromise are regarded as most likely having embolic or local perforator hemodynamic compromise and They are therefore unlikely to benefit from flow augmentation, and carry a low risk of recurrent stroke on medical therapy alone. Such medical therapy could include, for example, anticoagulants and/or antiplatelet agents. Patients with distal flow compromise, on the other hand, are regarded has having regional hemodynamic compromise with a high risk of stroke. These patients stand to potentially benefit from flow augmentation by endovascular or surgical means such as angioplasty/stenting or surgical bypass procedures, respectively.

1. System Description

FIG. 1 shows the components of an exemplary system appropriate for implementing the methods for assessing VBD as described herein. The system generates phase contrast magnetic resonance (PCMR) images (as well as possibly other data) which may be in a format such as DICOM (Digital Imaging and Communication in Medicine) which is a standard protocol for sending, receiving and storing medical images. The system includes an MRI system 101 as a source of the DICOM images generated for a particular patient. Additional imaging systems which use different imaging modalities such as CT (Computed Tomography), ultrasound, or conventional X-ray angiography may also be used to generate DICOM images or data. The imaging system or systems are connected via a local network to a DICOM storage device 120 such as a PACS (Picture Archiving and Communication System) that is widely used in the clinical and radiological environment. The PACS system provides the functionality of retrieving DICOM images in response to queries received over the network. The system also includes one or more user computers 130 where all or part of the data presentation and/or decision-making software resides. The user computer includes an input device (e.g., keyboard) and a device for displaying the data and/or images to a user (e.g., a monitor). The user computers 130 are connected with the PACS 120 via either a LAN (Local Area Network) or via the internet. (Alternatively, the PACS system may be incorporated into the user computer 130.) The decision making software can take several forms such as a stand-alone application, an added-on feature of existing medical imaging or management software, or an embedded applet within a web browser. The communication and interaction between user computers 130 and the PACS 120 may be based on internet protocols such as HTTP or HTTPS, depending on the requirement of security.

The system may be used to make quantitative flow measurements of the extracranial and intracranial arteries using quantitative phase contrast magnetic resonance angiography. In this technique, an axial 3-D time-of-flight MR angiography is first performed to obtain a three dimensional surface rendering of the vasculature, including the circle of Willis, and a perpendicular cut to the axis of the desired vessel is generated when a vessel is picked in the 3D image. A phase contrast MR scan is then performed using a bipolar gradient pulse directed transverse to the perpendicular cut to generate a phase image which represents blood velocity through the perpendicular cut. Blood flow may then be calculated based upon the cross-sectional area of the selected vessel. The system may be programmed to perform these steps automatically. The may be employed to evaluate patients as having symptomatic VBD by measuring blood flow at one or more sites distal to where disease may be expected to be present in the patient, including the basilar artery and the posterior cerebral arteries (PCAs), comparing a measured blood flow with a specified threshold, and classifying the patient as appropriate for receiving a flow augmentation therapy or as appropriate for receiving only medical therapy in accordance with whether the measured blood flow is below or above the specified threshold, respectively. The basilar and PCA blood flows are preferably measured using quantitative phase contrast magnetic resonance angiography as described above, but other methods could also be used. A decision-making algorithm for deciding whether a patient should be classified as appropriate for receiving a flow augmentation therapy or as appropriate for receiving only medical therapy is described in detail below.

2. Algorithm Description

Figure 2:
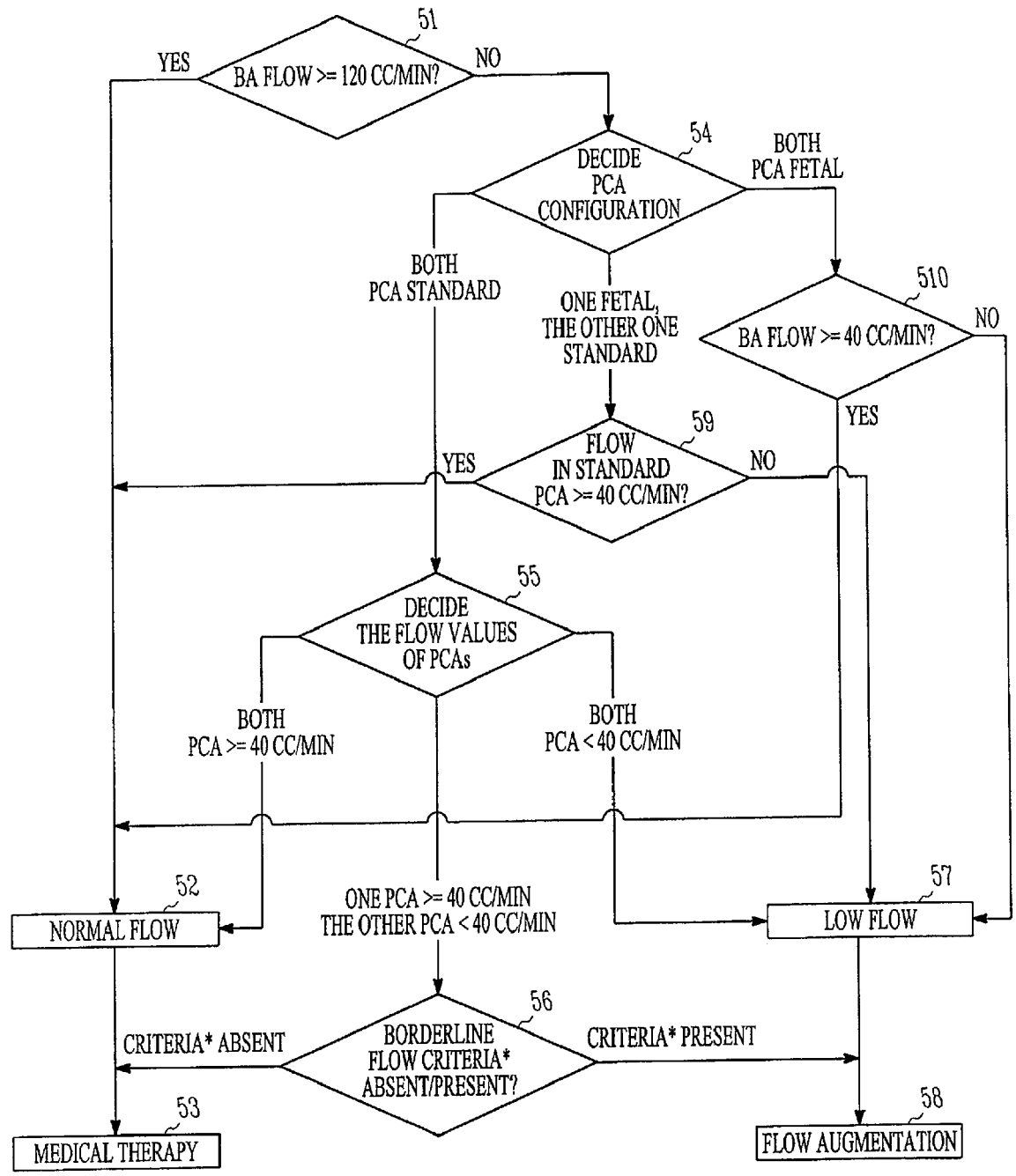
FIG. 2 illustrates an algorithm for evaluation of VBD.

FIG. 2 illustrates the steps involved in an exemplary decision-making algorithm for evaluating patients with symptomatic VBD, designated as steps S1 through S10. The algorithm may be performed manually but is preferably implemented in the programming of an appropriate processing element such as the user computer 130 in FIG. 1. The algorithm may also be contained in a storage medium for containing processor-executable instructions such as magnetic or optical media which may be transported to an appropriate processing device. At step S1, the measured basilar blood flow is compared with a specified basilar flow threshold, where exemplary values of the basilar flow threshold are 120 cc/min or 20% below that amount. If the measured basilar blood flow is above the specified basilar flow threshold, the patient is classified as having normal distal flow at step S2 and classified as appropriate for receiving only medical therapy at step S3. If the measured basilar blood flow is below the specified basilar flow threshold, the algorithm accepts a data input which specifies whether the configurations of the patient's posterior PCAs are normal or fetal at step S4. In approximately 30% of people, one or both PCAs take origin from the internal carotid artery (ICA) directly or via the posterior communicating artery. Direct origin from the ICA is termed a fetal PCA configuration as opposed to the normal configuration where the PCA originates from the basilar artery. The blood supply of a fetal PCA thus derives mostly from the anterior circulation.

If the configurations of both PCAs are normal, the PCA blood flows are compared with a specified PCA flow threshold at step S5. Exemplary PCA flow thresholds are 40 cc/min or 20% below that amount. The patient is classified as having normal flow at step S2 and appropriate for receiving only medical therapy at step S3 if a measured blood flow through each PCA is above the specified PCA flow threshold and classified as having low flow at step S7 and appropriate for receiving flow augmentation therapy at step S8 if a measured blood flow through each PCA is below a specified PCA flow threshold. If a measured blood flow through only one PCA is below the specified PCA flow threshold, a determination is made at step S6 whether additional specified criteria indicating a need for flow augmentation are met. The additional specified criteria indicating a need for flow augmentation may include one or more of the following: the basilar flow waveform oscillates around zero, the patient's symptoms are exacerbated with head position, anticoagulation/antiplatelet medication is contraindicated in the patient, the patient requires very elevated BP to avert symptoms, or the basilar flow is less than the specified PCA flow threshold.

If the measured basilar blood flow is below the specified basilar flow threshold and if the configuration of one PCA is normal while the configuration of the other PCA is fetal, the patient is classified as having low flow and as appropriate for receiving flow augmentation therapy if a measured blood flow through the PCA of normal configuration is below the specified PCA flow threshold as determined at step S9. Otherwise, the patient is classified as having normal flow and appropriate for receiving only medical therapy.

If the measured basilar blood flow is below the specified basilar flow threshold and if the configurations of both PCAs are fetal, the patient is classified as having low flow and as appropriate for receiving flow augmentation therapy if a measured blood flow through the basilar artery is also below the specified PCA flow threshold as determined at step S10. Otherwise, the patient is classified as having normal flow and appropriate for receiving only medical therapy.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A system for evaluating a patient identified as having symptomatic vertebrobasilar disease (VBD), comprising:
    means for measuring blood flow at one or more sites distal to where disease may be expected to be present in the patient, including the basilar artery and the posterior cerebral arteries (PCAs);
    a processing element which is programmed to:
    classify the patient as appropriate for receiving only medical therapy if the measured basilar blood flow is above a specified basilar flow threshold;
    if the measured basilar blood flow is below the specified basilar flow threshold, accept a data input which specifies whether the configurations of the patient's posterior PCAs are normal or fetal; and,
    if the configurations of both PCAs are normal, classify the patient as appropriate for receiving only medical therapy if a measured blood flow through each PCA is above a specified PCA flow threshold, classify the patient as appropriate for receiving flow augmentation therapy if a measured blood flow through each PCA is below a specified PCA flow threshold, and classify the patient as borderline if a measured blood flow through only one PCA is below the specified PCA flow threshold and additional specified criteria indicating a need for flow augmentation are met.

2. The system of claim 1 wherein the basilar flow threshold is 120 cc/min.

3. The system of claim 1 wherein the processing element is further programmed to classify the patient as appropriate for receiving flow augmentation therapy if the measured basilar blood flow is below the specified basilar flow threshold, the configurations of both PCAs are normal, a measured blood flow through only one PCA is below the specified PCA flow threshold, and additional specified criteria indicating a need for flow augmentation are met, wherein the additional specified criteria indicating a need for flow augmentation include one or more of the following: the basilar flow waveform oscillates around zero, the patient's symptoms are exacerbated with head position, anticoagulation/antiplatelet medication is contraindicated in the patient, the patient requires very elevated BP to avert symptoms, or the basilar flow is less than the specified PCA flow threshold.

4. The system of claim 1 wherein the processing element is further programmed to:
 if the measured basilar blood flow is below the specified basilar flow threshold and if the configuration of one PCA is normal while the configuration of the other PCA is fetal, classify the patient as appropriate for receiving flow augmentation therapy if a measured blood flow through the PCA of normal configuration is below the specified PCA flow threshold.

5. The system of claim 1 wherein the processing element is further programmed to:
 if the measured basilar blood flow is below the specified basilar flow threshold and if the configurations of both PCAs are fetal, classify the patient as appropriate for receiving flow augmentation therapy if a measured blood flow through the baslilar artery is also below the specified PCA flow threshold.

6. The system of claim 1 wherein the PCA flow threshold is 40 cc/min.

7. The system of claim 1 wherein the means for measuring blood flow is a quantitative phase contrast magnetic resonance angiography system.

8. A method comprising:
 identifying a patient as having symptomatic vertbrobasilar disease (VBD);
 measuring blood flow in the basilar artery and the posterior cerebral arteries (PCAs) of the patient;
 comparing a measured basilar blood flow with a specified basilar flow threshold;
 classifying the patient as appropriate for receiving medical therapy only if the measured basilar blood flow is above specified basilar flow threshold;
 if the measured basilar blood flow is below the specified basilar flow threshold, determining whether the configuration of the patient's posterior cerebral arteries (PCAs) is normal or fetal;
 if the configurations of both PCAs are normal, classifying the patient as appropriate for receiving only medical therapy if a measured blood flow through each PCA is above a specified PCA flow threshold, classifying the patient as appropriate for receiving flow augmentation therapy if a measured blood flow through each PCA is below a specified PCA flow threshold, and classifying the patient as borderline if a measured blood flow through only one PCA is below the specified PCA flow threshold and additional specified criteria indicating a need for flow augmentation are met;
 if the measured basilar blood flow is below the specified basilar flow threshold and if the configuration of one PCA is normal while the configuration of the other PCA is fetal, classifying the patient as appropriate for receiving flow augmentation therapy if a measured blood flow through the PCA of normal configuration is below the specified PCA flow threshold; and,
 if the measured basilar blood flow is below the specified basilar flow threshold and if the configurations of both PCAs are fetal, classifying the patient as appropriate for receiving flow augmentation therapy if a measured blood flow through the basilar artery is also below the specified PCA flow threshold; and,
 displaying the result of the classifying step.

9. A storage medium containing processor-executable instructions for performing a method comprising:
 accepting as a data input the measured blood flow at one or more sites distal to where vertebrobasilar disease may be expected to be present in a patient, including the basilar artery and the posterior cerebral arteries (PCAs);
 comparing a measured blood flow with a specified threshold; and
 classifying the patient as appropriate for receiving a flow augmentation therapy or as appropriate for receiving only medical therapy in accordance with whether the measured blood flow is below or above the specified threshold, respectively.

10. The storage medium of claim 9 further comprising instructions for classifying the patient as appropriate for receiving a flow augmentation therapy or as appropriate for receiving medical therapy only in accordance with whether the measured basilar blood flow is below or above a specified basilar flow threshold, respectively.

11. The storage medium of claim 10 wherein the basilar flow threshold is 120 cc/min.

12. The storage medium of claim 9 further comprising instructions for:
 classifying the patient as appropriate for receiving only medical therapy if the measured basilar blood flow is above a specified basilar flow threshold;
 if the measured basilar blood flow is below the specified basilar flow threshold, accepting a data input which specifies whether the configurations of the patient's posterior PCAs are normal or fetal; and,
 if the configurations of both PCAs are normal, classifying the patient as appropriate for receiving only medical therapy if a measured blood flow through each PCA is above a specified PCA flow threshold, classifying the patient as appropriate for receiving flow augmentation therapy if a measured blood flow through each PCA is below a specified PCA flow threshold, and classifying the patient as borderline if a measured blood flow through only one PCA is below the specified PCA flow threshold and additional specified criteria indicating a need for flow augmentation are met.

13. The storage medium of claim 12 further comprising instructions for classifying the patient as appropriate for receiving flow augmentation therapy if the measured basilar blood flow is below the specified basilar flow threshold, the configurations of both PCAs are normal, a measured blood flow through only one PCA is below the specified PCA flow threshold, and additional specified criteria indicating a need for flow augmentation are met, wherein the additional specified criteria indicating a need for flow augmentation include one or more of the following: the basilar flow waveform oscillates around zero, the patient's symptoms are exacerbated with head position, anticoagulation/antiplatelet medication is contraindicated in the patient, the patient requires very elevated BP to avert symptoms, or the basilar flow is less than the specified PCA flow threshold.

14. The storage medium of claim 12 further comprising instructions for:
   if the measured basilar blood flow is below the specified basilar flow threshold and if the configuration of one PCA is normal while the configuration of the other PCA is fetal, classifying the patient as appropriate for receiving flow augmentation therapy if a measured blood flow through the PCA of normal configuration is below the specified PCA flow threshold.

15. The storage medium of claim 12 further comprising instructions for:
   if the measured basilar blood flow is below the specified basilar flow threshold and if the configurations of both PCAs are fetal, classifying the patient as appropriate for receiving flow augmentation therapy if a measured blood flow through the baslilar artery is also below the specified PCA flow threshold.

16. The storage medium of claim 12 wherein the PCA flow threshold is 40 cc/min.

* * * * *